(12) United States Patent
Nadau Fourcade

(10) Patent No.: US 10,688,117 B2
(45) Date of Patent: Jun. 23, 2020

(54) TOPICAL WASH COMPOSITION FOR USE IN ACNE PATIENTS

(71) Applicant: Galderma S.A., Cham (CH)

(72) Inventor: Karine Nadau Fourcade, Villeneuve Loubet (FR)

(73) Assignee: GALDERMA S.A., Cham (CH)

( * ) Notice: Subject to any disclaimer, the term of this patent is extended or adjusted under 35 U.S.C. 154(b) by 0 days.

(21) Appl. No.: 15/955,371

(22) Filed: Apr. 17, 2018

(65) Prior Publication Data

US 2019/0076453 A1  Mar. 14, 2019

Related U.S. Application Data

(63) Continuation of application No. 14/122,955, filed as application No. PCT/EP2012/060072 on May 29, 2012, now abandoned.

(60) Provisional application No. 61/490,850, filed on May 27, 2011.

(30) Foreign Application Priority Data

Sep. 30, 2011 (FR) .................................... 11 58869

(51) Int. Cl.
| | |
|---|---|
| *A61K 31/704* | (2006.01) |
| *A61K 8/365* | (2006.01) |
| *A61K 8/63* | (2006.01) |
| *A61K 31/191* | (2006.01) |
| *A61K 31/56* | (2006.01) |
| *A61Q 19/10* | (2006.01) |
| *A61K 33/30* | (2006.01) |
| *A61K 8/46* | (2006.01) |
| *A61K 8/27* | (2006.01) |
| *A61K 31/19* | (2006.01) |
| *A61K 31/315* | (2006.01) |

(52) U.S. Cl.
CPC .............. *A61K 31/704* (2013.01); *A61K 8/27* (2013.01); *A61K 8/365* (2013.01); *A61K 8/463* (2013.01); *A61K 8/466* (2013.01); *A61K 8/63* (2013.01); *A61K 31/19* (2013.01); *A61K 31/191* (2013.01); *A61K 31/315* (2013.01); *A61K 31/56* (2013.01); *A61K 33/30* (2013.01); *A61Q 19/10* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 3,141,821 A | 7/1964 | Compeau | |
| 3,535,422 A | 10/1970 | Cox et al. | |
| 4,056,611 A | 11/1977 | Young | |
| 5,635,469 A | 6/1997 | Fowler et al. | |
| 6,403,110 B1 | 6/2002 | Siddiqui et al. | |
| 2002/0111281 A1 | 8/2002 | Vishnupad | |
| 2002/0197228 A1 | 12/2002 | LaSala et al. | |
| 2004/0156873 A1 | 8/2004 | Gupta | |
| 2008/0193405 A1* | 8/2008 | Mukherjee | A61K 8/0212 424/70.16 |
| 2009/0035233 A1 | 2/2009 | Spindler et al. | |
| 2010/0143285 A1 | 6/2010 | Mallard et al. | |
| 2010/0160439 A1 | 6/2010 | Mallard | |
| 2010/0221245 A1 | 9/2010 | Kunin | |
| 2010/0226948 A1 | 9/2010 | Jitpraphai et al. | |
| 2011/0045037 A1 | 2/2011 | Tamarkin et al. | |

FOREIGN PATENT DOCUMENTS

| | | |
|---|---|---|
| CN | 101288640 A | 10/2008 |
| EP | 0981325 B1 | 10/2004 |
| EP | 2005942 A1 | 12/2008 |
| FR | 2804321 A1 | 8/2013 |
| JP | 2009517429 A | 4/2009 |
| KR | 20110030812 A | 3/2011 |
| WO | 98/51275 A1 | 11/1998 |
| WO | 2007/062995 A2 | 6/2007 |
| WO | 2010063674 A1 | 6/2010 |
| WO | 2011007183 A2 | 1/2011 |
| WO | WO-2012/001082 A2 | 1/2012 |

OTHER PUBLICATIONS

International Search Report dated Jun. 11, 2013 by the European Patent Office as the International Searching Authority in corresponding International Patent Application No. PCT/EP2012/060072, 5 pp.
Kawakami et al., JP 10-316555 A A, 1998, machine translation. Retrieved on Jun. 27, 2016 from https://dossier1.j-platpat.inpit.go.jp/tri/all/odse/ODSE_GM101_Top.action.
Bigotti et al., "Zinc and its Derivatives: Their Applications in Cosmetic", J. Appl. Cosmetol., (2005), vol. 23, pp. 139-147.
Hibbs, J., "Anionic surfactants", Chemistry and Technology of Surfactants, Ch. 4, vol. 91.
Robinson et al., "Final report of the amended safety assessment of sodium laureth sulfate and related salts of sulfated ethoxylated alcohols", International Journal of Toxicology, vol. 29(4 suppl), pp. 151S-161S.
Cosmetics & Toiletries Formulations Database; "Product: Acne Cleanser"; William Andrew Publishing; 2005; (Abstract only).
Cosmetics Business, "in-cosmetics 2009—the cream of the crop"; Apr. 18, 2010; retrieved from: https://www.cosmeticsbusiness.com/news/article_page/incosmetics_2009_the_cream_of_the_crop/492 83; 11 pages.

(Continued)

*Primary Examiner* — Dale R Miller

(74) *Attorney, Agent, or Firm* — Foley & Lardner LLP; Sunit Talapatra

(57) ABSTRACT

Wash compositions for topical application are described. The compositions can be stable and well tolerated. Also described, are methods of using such compositions as cosmetic or pharmaceutical products. For example, the compositions can be used for cleansing the skin, preferably of acne patients, without compromising the skin barrier or resulting in over-compensation of sebum production. A topical wash composition is also described that can include: a) at least one surfactant; b) a zinc salt of gluconic acid; and c) a salt or derivative of glycyrrhizic acid or of glycyrrhetinic acid.

21 Claims, No Drawings

(56) References Cited

OTHER PUBLICATIONS

Dermastir, "Cosmetic Ampoules—Zinc Gluconate", retrieved from: "https://www.dermastir.com/skincare-shop/dermastir-ampoules-zinc-gluconate", first published on internet Dec. 15, 2006.

Harvey M. Fishman, "The Mild Surfactant Is Ideal for Body Care"; retrieved from: https://www.happi.com/contents/view_gleams-and-notions/2011-04-05/this-mild-surfactant-is-ideal-for-body-care-80722; Apr. 5, 2011.

International Search Report and Written Opinion issued in International Application No. PCT/EP2013/073738, dated Mar. 3, 2014.

International Search Report and Written Opinion issued in International Application No. PCT/EP2013/073737, dated Mar. 3, 2014.

Pascoe, "Cetaphil DermaControl Oil Control Foam Wash and Moisturizer for Oily Skin" Rosacea Support Group, Apr. 26, 2012, downloaded on Jul. 20, 2017 from "rosacea-support.org/cetaphil-dermacontrol-oil-control-foam-wash-and-moisturizer-for-oilyskin.html", 4 pages.

Tanghetti et al., "A Current Review of Topical Benzoyl Peroxide: New Perspectives on Formulation and Utilization", Dermatologic Clinics, Jan. 2009, vol. 27(1 ), pp. 17-24.

Truth in Aging, "Dipotassium glycyrrhizate", truthinaging.com, captured by Internet Archive Waybackmachine on Oct. 26, 2011, retrieved from "https://web.archive.org/web/20111026213509/https://www.truthinaging.com/ingredients/dipotassium-glycyrrhizate".

\* cited by examiner

TOPICAL WASH COMPOSITION FOR USE IN ACNE PATIENTS

CROSS-REFERENCE TO PRIOR APPLICATIONS

This application is a continuation of application Ser. No. 14/122,955, filed Jan. 16, 2014, which is a National Stage of PCT/EP2012/060072, filed May 29, 2012, and designating the United States (published in English on Dec. 6, 2012, as WO 2012/163928 A2), which claims priority under 35 U.S.C. § 119 to U.S. Provisional Patent Application No. 61/490,850, filed May 27, 2011, and French Patent Application No. FR 1158869, filed Sep. 30, 2011, each hereby expressly incorporated by reference in its entirety and each assigned to the assignee hereof.

The present invention relates to wash compositions for topical application, stable and well tolerated and to their uses thereof as cosmetic or pharmaceutical products, said compositions being used for cleansing the skin, preferably of acne patients, without compromising the skin barrier or resulting in over-compensation of sebum production.

Acne is a common multi-factor pathology that attacks skin rich in sebaceous glands (face, shoulder area, arms and intertriginal areas). It is the most commonly occurring form of dermatosis. The following five pathogenic factors play a determining role in the formation of acne:
1. genetic predisposition;
2. overproduction of sebum (seborrhoea);
3. androgens;
4. follicular keratinization disorders (comedogenesis); and
5. bacterial colonization and inflammatory factors.

There are several forms of acne, the common factor of all being attack of the pilosebaceous follicles. Mention may be made in particular of acne conglobata, cheloid acne of the nape of the neck, acne medicamentosa, recurrent miliary acne, necrotic acne, neonatal acne, premenstrual acne, occupational acne, acne rosacea, senile acne, solar acne and common acne.

Common acne, also known as polymorphic juvenile acne, is the most common. It comprises four stages:
- stage 1 corresponds to comedonic acne characterized by a large number of open and/or closed comedones and of microcysts;
- stage 2, or papulopustular acne, is of mild to moderate seriousness. It is characterized by the presence of open and/or closed comedones, of microcysts, but also of red papules and pustules. It mainly affects the face and leaves few scars;
- stage 3, or papulocomedonic acne, is more serious and extends to the back, the chest and the shoulders. It is accompanied by a large number of scars;
- stage 4, or nodulocystic acne, is accompanied by numerous scars. It exhibits nodules and also painful voluminous crimson pustules.

The various forms of acne described above can be treated with active agents such as anti-seborrheic agents and anti-infectives, for example benzoyl peroxide (in particular the product Eclaran® sold by the company Pierre Fabre), with retinoids such as tretinoin (in particular the product Retacnyl® sold by the company Galderma) or isotretinoin (the product Roaccutane® sold by Laboratoires Roche), or else with naphthoic acid derivatives. Naphthoic acid derivatives such as, in particular, 6-[3-(1-adamantyl)-4-methoxyphenyl]-2-naphthoic acid, which is commonly called adapalene (the product Différine® sold by the company Galderma), are widely described and recognized as active ingredients that are just as effective as tretinoin for the treatment of acne.

Some Adverse Events (AE) appear with Rx (with prescriptions) products (mainly retinoids topical/oral) and produce important related AE and frequent cutaneous side effects such as Ziana: 27% subjects with related application site AE and the most important is dry skin.

In a general manner, anti-acne therapies can provoke dry skin, that can be due to skin barrier damage, leading to an increased loss of water from the stratum corneum (TEWL: Trans Epidermal Water Loss). An intact skin barrier is therefore essential for the correct functioning of both the physical and chemical elements of the skin's protective actions. Acne directly influences the skin barrier function via the inflammatory process and sebum overproduction. Excessive sebum production leads to imbalanced skin lipids and structural alterations in key barrier components such as fatty acids deficiency and also depletion of cholesterol and ceramides which in turn leads to an increased TEWL. Skin barrier damage and increased TEWL can aggravate acne. Consequently dermatologists recognise the value of moisturizers and cleansers as adjuncts to prescribed treatments.

Skin Care regimen recommended by dermatologists for acne treatment encompasses the following steps:
- Step 1: Wash
- Step 2: Medicate (Rx treatment)
- Step 3: Hydrate & Protect It is useful to have Skin Care Products which improve Acne Signs/Symptoms.

The present invention related to a composition to be used in the step 1 as a wash product. While cleansing does not directly address the causal mechanism behind acne, it is considered that good skin care involving daily cleansing is an important part of attaining dermatological health in patients with acne.

There is often a tendency among acne sufferers to "over clean". Many use astringent washes, scrubs and abrasives in an attempt to thoroughly remove sebum and dirt. Harsh cleansing is harmful to acne skin, particularly when undergoing medical treatments that provide further insults to the already compromised skin barrier. Over cleansing may stimulate overproduction of sebum and thereby may increase the severity of acne.

One objective of the present invention is to provide a topical dermatological/pharmaceutical wash composition stable and well tolerated, that effectively cleanses the skin of acne patients, without compromising the skin barrier or resulting in over-compensation of sebum production. Thus, in one embodiment, the present invention provides composition to reduce side effects of Acne such as decrease adverse events secondary to acne treatments (reduce Dry skin; decrease erythema; reduce stinging/burning).

Surprisingly the patentee has found that the composition comprising at least:
a) one surfactant,
b) a zinc salt of gluconic acid,
c) a salt or derivative of glycyrrhizic acid or of glycyrrhetinic acid.
answers to the following needs:
Washing/cleansing the skin,
Formulation that regulates sebum,
With a non-comedogenic action,
Maintain the integrity of the skin barrier, and
With one additional action as required for patient acceptability: a foaming action.

To achieve the cleansing action, the present invention requires the presence of at least one surfactant. To confer good tolerability and no irritancy, i.e. to keep the integrity of the skin barrier, man skilled in the art knows that non-ionic surfactant are the well tolerated surfactants and could be used. However, these latter have no good foaming properties. Surfactants known to have good foaming properties have the drawbacks of being irritant. The first problem to be solved is to find the right surfactants which confer to the composition, the cleansing properties as well as the good tolerability and the required foaming action.

As a solution to the problem to be solved in the invention, the present invention provides compositions with new generations of mild anionic surfactants adapted to acne and sensitive skin, to provide a soap free, foaming wash cleansing composition according to the invention. According to the invention, Surfactants are considered to be mild when their application results in minimal swelling, binding and irritation of the skin. Sodium lauryl sulfate is often selected as a reference example of an irritating surfactant. A mild surfactant is less irritant than sodium lauryl sulfate but also sodium lauryl ether sulfate.

An anionic surfactant according to the invention is designated as such due to the presence of a negatively charged part. The general form of an anionic surfactant is $RX^-M^+$ Where R is the carbon chain length, M is the neutralizing group (such as sodium, potassium, magnesium, zinc, ammonium, triethanolamine), X is the negatively charged species which can be any of the following: carboxylate, sulfonate, sulfate or phosphate.

These surfactants have detergent and/or cleansing properties. The mild anionic surfactants are more specifically selected from the following list, used alone or in combination:

carboxylate derivatives such as alkyl isethionates or acyl isethionates (salts of sodium, potassium, ammonium or magnesium) like sodium cocoyl isethionate sold by clariant with the trade name Hostapon SCI-85G or lauroyl methyl isethionate called Iselux from Innospec, Amino acids and Acyl amino acids such as glutamate, acyl glutamate:lauroyl glutamate called Protelan AGL 95 sold by Zschimmer & Schartz, sodium capryloyl glutamate also sold by Zschimmer and Schartz and called Protelan AG8, sarcosinate or acyl sarcosinate such as sodium lauroyl sarcosinate called Protelan LS9011 sold by Zschimmer & Schartz, glycinate or acyl glycinate such as cocoyl glycinate called Hostapon SG from Clariant, fatty acid arginate, alaninate or acyl alaminate, acyl peptides, cocoyl apple amino acid such as Proteol APL from SEPPIC, lactylates or acyl lactylates, sodium lauryl glucose carboxylate (plantapon LGC sorb from Cognis), sodium laureth-13 carboxylate.

Sulfate derivatives:

Alkyl sulfates, alkyl ether sulfates, alkylamido ether sulfates, alkylarylpolyether sulfates, monoglyceride sulfates such as zinc coceth sulfate sold by Zschimmer & Schartz with the trade name Zetesol ZN, Sulfonate derivatives:

alkyl sulfonates, alkylamidesulfonates, alkylarylsulfonates, α-olefinsulfonates and preferentially $C_{14}$-$C_{16}$ α-olefinsulfonates preferably its sodium salt such as Hostapur OSB from Clariant, paraffinsulfonates, alkyl sulfosuccinates such as dioctyl sodium sulfosuccinate also known under the name sodium docusate, alkyl ether sulfosuccinates, alkylamidesulfosuccinates; alkyl sulfoacetates; alkyl taurates or acyl taurates such as fatty acid methyl taurate, sodium methyl cocoyl taurate sold by Seppic with the trade name Somepon T25

Phosphates:

alkyl ether phosphates, alkyl phosphates

In a preferred embodiment, the present invention provides compositions with new generation of very mild surfactants adapted to acne and sensitive skin and selected from the following to be used alone or in combination: zinc coceth sulfate, sodium cocoyl isethionate, sodium lauroyl methyl isethionate, sodium methyl cocoyl taurate, $C_{14}$-$C_{16}$ α-olefinsulfonates preferably its sodium salt or amino acid derivatives such as sodium lauroyl sarcosinate or sodium lauroyl glutamate.

More preferably, the anionic surfactant used in the composition is zinc coceth sulfate, the zinc part of it having a soothing, anti-irritating and astringent effect, beneficial for the use of the composition of the invention.

Accordingly, the anionic surfactants have a concentration between 0.25% and 20% expressed by weight of active material (AM) relative to the total weight of the composition. In a preferred embodiment the anionic surfactants concentration expressed by weight of active matter (AM) relative to the total weight of the composition is between 1 and 15% AM. Active material refers to the percentage of pure surfactant included in a formulation. In many cases commercially available surfactants are sold as aqueous solutions. The amount of AM can vary upon the amount of water used to dilute the neat surfactant and the grade of raw material supplied from commercial vendors.

In a preferred embodiment the anionic surfactant is zinc coceth sulfate, in a concentration between 0.25% and 20% expressed by weight of active matter (AM) relative to the total weight of the composition. Preferably, the concentration expressed by weight of active material (AM) relative to the total weight of the composition for zinc coceth sulfate is between 1% and 15% AM, preferably between 2% and 8%.

One skilled in the art may use various commercial products containing zinc coceth sulfate proposed in various dilutions. Some specific commercial products propose Zinc coceth sulfate in solution at 25% such as Zetesol ZN from Zschimmer & Scharz expressed by weight of active material (AM) relative to the total weight of the solution. Consequently, in an alternative preferred embodiment, the quantity of said zinc coceth sulfate (Zetesol ZN) expressed by weight relative to the total weight of the composition is between 5% and 40% and preferred to be 19.5%.

In the composition according to the invention, one skilled in the art will therefore adapt the right concentration of the commercial surfactant to be used in the composition to reach the exact needed concentration between 1% and 10% of active matter relative to the total weight of the composition.

According to the invention, the composition comprises also zinc gluconate.

Zinc gluconate (also called *Zincum gluconium*) is the zinc salt of gluconic acid. It is an ionic compound consisting of two moles of gluconate for one mole of zinc. Zinc gluconate is a popular form for the delivery of zinc as a dietary supplement.

Gluconic acid is found naturally, and is industrially manufactured by the fermentation of glucose, typically by *Aspergillus niger*, but also by other fungi, e.g. *Penicillium*, or by bacteria, e.g. *Acetobacter, Pseudomonas* and *Gluconobacter*. In its pure form, it is a white to off-white powder. It can also be manufactured by electrolytic oxidation, although this is a more expensive process. The advantages are a lower microbiological profile, and a more complete reaction, yielding a product with a longer shelf life.

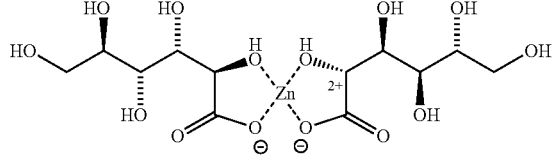

In a preferred embodiment, the concentration of zinc gluconate expressed by weight relative to the total weight of the composition is between 0.1% and 1%, preferably between 0.15% and 0.3%, more preferably 0.2%.

According to the invention, the composition also contains a salt or derivative of glycyrrhizic acid or of glycyrrhetinic acid.

Glycyrrhizic acid is derived from the plant *Glycyrrhiza glabra*, or liquorice root, it is reputed to provide anti-irritant and anti-inflammatory properties. The soothing and calming properties of liquorice extracts make them interesting candidates for inclusion in treatments for sensitive skin conditions such as eczemas, erhythema, seborric dermatitis and itching.

Glycyrrhetinic acid is a pentacyclic triterpenoid derivative of the beta-amyrin type obtained from the hydrolysis of glycyrrhizic acid (alternative names: glycyrrhizin or glycyrrhizinic acid), which was obtained from the herb liquorice. It is used in flavoring and it masks the bitter taste of compounds like aloe and quinine. It is effective in the treatment of peptic ulcer and also has expectorant (antitussive) properties. It has some additional pharmacological properties including antiviral, antifungal, antiprotozoal, and antibacterial activities.

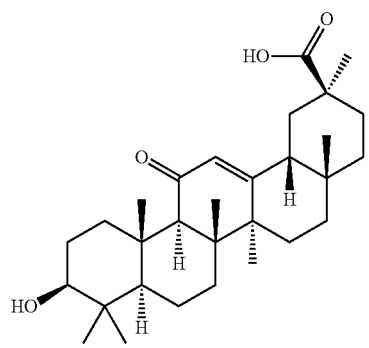

Chemical Structure of Glycyrrhetinic Acid

As salts and derivatives we can cite potassium salt, sodium salt, monoammonium salt, ammonium glycyrrhiziate, succinate disodium, dipotassium salt of glyccyrrhizic acid (Dipotassium Glycyrrhizate) or esters of said acid such as glycerin monoester.

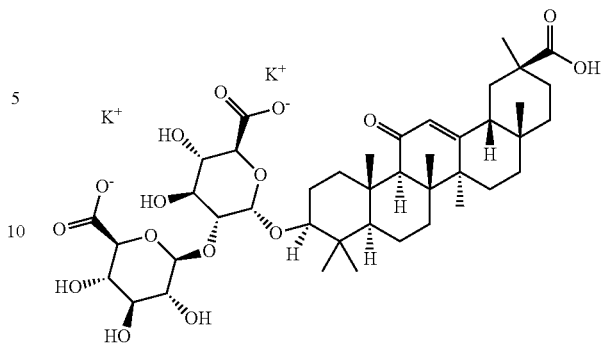

Chemical Structure of Dipotassium Glycyrrhizate

In a preferred embodiment, the glycyrrhetinic derivative is dipotassium glycyrrhizate at a concentration expressed by weight relative to the total weight of the composition between 0.1% and 1%, preferably between 0.15% and 0.3%, more preferably 0.25%.

Thus one aspect of the present invention is a composition, comprising:
a) one surfactant,
b) a zinc salt of gluconic acid,
c) a salt or derivative of glycyrrhizic acid or of glycyrrhetinic acid.

More preferably, the composition of the invention comprises, in a cosmetic acceptable carrier, the combination of:
a) at least one mild anionic surfactant
b) zinc gluconate
c) dipotassium glycyrrhizate.

The composition has the advantage to cleanse the skin, but also to help to regulate sebum production and soothe the skin and solve the problems previously described.

The composition is for topical application and can be of any type as known by one skilled in the art.

As non limiting examples of type of composition, the composition can be in the form of a solution, a gel or an emulsion. When a gel form is preferred, the composition contains as an additional constituent some gelling agents, like for example microcrystalline cellulose, sodium carboxymethyl cellulose, the "electrolyte-insensitive" carbomers such as Carbopol ETD2020™ sold by the company Noveon, polysaccharides, non limiting examples of which include xanthan gum or gellan gum or pectin, the family of magnesium aluminium silicate, Sodium magnesium silicate, sodium magnesium fluorosilicate, magnesium sodium silicate and tetrasodium pyrophosphate company, hydroxypropylmethylcellulose, the family of acrylic polymers, acrylates copolymer sold under names Aqua SF1 by Noveon-lubrizol, polyacrylate-1 crosspolymer (Aqua CC by Npveon), Acrylates crosspolymer 4 (Aqua SF2 by Noveon) or acrylates/beheneth-25 bethacrylate copolymer sold under trade name Novethix L-10, polymer polyacrylate-13 and polyisobutene and polysorbate 20 sold under the name SEPIPLUS 400 by the company Seppic, and gelling agents of the polyacrylamide family such as sodium acryloyl-dimethyltaurate copolymer/isohexadecane/polysorbate 80 mixture sold under the name Simulgel 600PHA™ by the company Seppic, or the polyacrylamide/isoparaffin C13-14/laureth-7 mixture such as, for example, that sold under the name Sepigel 305™ by the company Seppic, by the, hydroxyethyl acrylate/sodium acryloyl dimethyl taurate copolymer under the name SEPINOV EMT 10 by the company Seppic, and the family of modified starches such as the modified potato starch sold under the name Structure Solanace™, or mixtures thereof or viscosity increasing agent such as sodium chloride or mixture that have synergic effect on the viscosity of anionic surfactants such as PEG-120 methyl glucose Dioleate, PEG-200 hydrogenated glyceryl palmate (and) PEG-7 glyceryl cocoate or ceteareth-60 myristyl glycol.

When an emulsion form is preferred, the composition contains, in addition to the anionic surfactant, zinc gluconate and dipotassium glycyrrhizate, at least one emulsifier and an oily phase that can be mixture of mineral, synthetic or silicone oils More, preferably, according to the invention, the composition is in the form of aqueous, aqueous-alcoholic or hydro-alcoholic solution.

According to a preferred embodiment, the composition is in the form of a solution and comprises an aqueous phase as a main constituent of the carrier. The aqueous phase may be present in an amount between 10 and 99% by weight relative to the total weight of the composition, preferably between 50 and 95% by weight and preferentially comprise water. This water can be purified water, floral water such as cornflower water, or a natural spring or mineral water, for example selected from water from Vittel, waters from the Vichy basin, water from Uriage, the water from La Roche Posay, Avene water or water from Aix les Bains.

As previously indicated, the composition of the invention required foaming properties. The patentee has found that to confer particular good foaming properties, the composition can be used with a specific packaging. In such packaging, the actuation of mechanical pump applies the required conditions to transform the liquid wash formulation into a foam product. In order to produce a foam the liquid wash formulation must pass through a mix chamber, where it is blended with air as it passes through one or more sieves. In general, as the sieve diameter decreases the density of the foam increases. Furthermore, lower viscosity formulations tend to mix more efficiently with air in the air chamber and form larger quantities of foam. An example of such a mechanical pump is the Rexam M3-S10 MINI FOAMER, as sold by Rexam-Pulvorex-Rieke company.

In another embodiment, the pH of the invention is well controlled and is between 2 and 7 preferably between 3 and 6, more preferably around 4.

In healthy skin, typical surface pH is between pH5 and pH6; however, in pathological acne skin surface pH is more basic. The pH gradient within the stratum corneum (SC) is an important factor for regulating several of the skin's homeostatic barrier functions. The pH of the healthy SC has a protective function against the growth of pathogenic bacteria and controls the balance of normal skin microflora including P. acnes. Skin pH is affected by a great number of factors and one key element is the pH of topically applied detergent products. The composition of the invention possesses a relatively low pH, which presents the benefit of helping the skin to restore its natural acidity and thus contributing to control the growth of microorganisms. Surprisingly the composition of the invention keeps the pH of the skin surface stable over the period of use of the composition.

The invention also provides a method for improving and/or preventing and/or inhibiting dermatological conditions linked to acne treatment. The invention also provides a treatment process for embellishing the skin or its surface appearance, is applied to the skin and/or its integument annexes. In a preferred embodiment, the treatment of skin is for skin with an acneic tendency or for combating the greasy appearance of the skin or the hair.

Throughout the present text, unless otherwise specified, it is understood that, when concentration ranges are given, they include the upper and lower limits of said range. Similarly, unless otherwise indicated, the proportions of the various constituents of the composition are expressed as percentage by weight (mass/mass [m/m] or weight in weight [w/w]) of the total weight of said composition.

The term "topical application" is intended to mean application to the skin or the mucous membranes.

The composition according to the invention may further comprise at least one of the following additives mentioned as an example, used in the composition alone or in combination:

Antioxidants such as vitamin E and its derivatives, such as DL alpha tocopherol or tocopherol acetate from Roche, vitamin C and its derivatives, as ascorbyl palmitate (Roche), butylated hydroxytoluene sold under the name Nipanox BHT by Clariant, butylated hydroxyanisole, acetyl cysteine, citric acid, sodium metabisulfite and/or sodium sulfite.

vitamins such as vitamin $B_3$ (vitamin PP) or niacinamide

Soothing agents and/or anti-irritants such as PPG-12/SMDI copolymer marketed by Bertek Pharmaceuticals under the trade name Polyolprepolymer-2 or allantoin or its derivatives or hyaluronic acid, Polyquaternium-51 such as lipidure PMB sold by Rossow, D-panthenol, aloe vera Lecithins, such as phosphatidyl choline, phosphatidyl inositol, phosphatidyl ethanolamine, and phosphatidic acid. An example of commercially available phospholipid used in the pharmaceutical industry is Phospholipon 90H which is supplied by Phospholipid GMBH.

Cholesterol or Cholesterol derivatives such as cholesterol esters.

Preservatives: such as benzalkonium chloride, bronopol, chlorhexidine, chlorocresol and its derivatives, ethyl alcohol, phenoxyethanol, potassium sorbate, sodium benzoate diazolidinylurea, benzyl alcohol, parabens or mixtures thereof methyl paraben sold under the name Nipagin M by Clariant, Propyl paraben sold under the name Nipasol by Clariant, mixture of parabens also sold by Clariant under the trade name Nipastat.

acids or bases such as citric acid, lactic acid, sodium citrate, triethanolamine, aminomethyl propanol, sodium hydroxide, diisopropanolamine, chelating agents such as EDTA or its salts with for example Disodium EDTA, Humectants such as propylene glycol, glycerin, pentylene glycol, 1-2 hexandiol or caprylyl glycol.

wetting agents such as poloxamers and/or glycols families and more particularly Synperonic PE/L44 and/or Synperonic PE/L62 and/or compounds such as propylene glycol, dipropylene glycol, propylene glycol dipelargonate, lauroglycol, ethoxydiglycol, sodium docusate.

Foam booster selected from, but not restricted to, polyethylene glycol such as for example PEG-75, or glycerylmonocaprylate (Imwitor 308 from Sasol), cocamidopropyl hydroxysultaine (Mirataine CBS from Rhodia), Sorbitan sesquicaprylate (Antil soft SC from Evonick) used in the composition alone or in combination.

Ingredients providing a smoothness of the foam selected from PEG-7 glyceryl cocoate, PEG 200 hydrogenated glyceryl palmate (Antil 200 from Evonick), Polypropylene Terephtalate (Aristoflex PEA from Clariant), C12-13 Alkyl Lactate (Cosmacol ELI from Sasol) used in the composition alone or in combination.

Perfume solubilising agents such PEG-40 hydrogenated castor oil, PEG-60 hydrogenated castor oil, polysorbate 80, polysorbate 20. —Perfume or ingredients providing fragrance to the composition such as natural or essential oils Refatting agents such as Lamesoft PO 65 from Cognis (coco-glucoside and glyceryl oleate) softigen 767 (PEG-6-Caprylic/Capric Glycerides) from Sasol.

The additives are present in the composition of the invention in proportions ranging from 0 to 20% by total weight of the composition.

The invention concerns also the use of the composition to wash skin of acne patients both under active treatments and in long-term maintenance.

The invention relates to the use of the composition to wash acne skin, wherein the barrier function of the skin is intact.

The invention relates also to the use of the composition to regulate the sebum production, to maintain a healthy pH of the skin.

The present invention will now be illustrated by means of the following examples, which cannot limit the scope of the present invention.

EXAMPLES

Example 1

| Composition | % |
| --- | --- |
| Purified water | QSAD 100 |
| Zinc coceth sulfate (25% in water) | 19.50 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| PEG-75 | 2 |
| Sodium benzoate | 0.20 |
| Disodium EDTA | 0.10 |
| PEG-40 hydrogenated castor oil | 0.25 |
| Fragrance | 0.25 | pH = 4.62

Example 2

| Composition | % |
| --- | --- |
| Purified water | QSAD 100 |
| Zinc coceth sulfate (25% in water) | 19.50 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| PEG-75 | 2 |
| Sodium benzoate | 0.20 |
| Disodium EDTA | 0.10 |
| PEG-40 hydrogenated castor oil | 0.25 |
| Coco-glucoside/glyceryl oleate | 2 |
| Glycerylmonocaprylate | 1 |
| Polyquaternium-51 | 0.2 | pH = 4.25

Example 3

| Composition | % |
| --- | --- |
| Purified water | QSAD 100 |
| Sodium methyl lauroyl isethionate (85% purity) | 4 |
| Zinc coceth sulfate (25% in water) | 8 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| PEG-75 | 2 |
| Sodium benzoate | 0.20 |
| Disodium EDTA | 0.10 |
| Citric acid | 0.15 | pH = 4.10

Example 4

| Composition | % |
| --- | --- |
| Purified water | QSAD 100 |
| Sodium C14-C16 olefin sulfonate | 5 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| Cocamidopropyl hydroxysultaine | 1 |
| Sorbitan sesquicaprylate | 0.30 |
| Sodium benzoate | 0.20 |
| Disodium EDTA | 0.10 |
| PEG-40 hydrogenated castor oil | 0.25 |
| Fragrance | 0.25 |

Example 5

| Composition | % |
| --- | --- |
| Purified water | QSAD 100 |
| Sodium cocoyl apple amino acid (32% in water) | 16 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| PEG-75 | 2 |
| Sodium benzoate | 0.20 |
| Disodium EDTA | 0.10 |
| PEG-40 hydrogenated castor oil | 0.25 |
| Fragrance | 0.25 |

Example 6

| Composition | % |
| --- | --- |
| Purified water | QSAD 100 |
| Zinc coceth sulfate (25% in water) | 10 |
| Sodium lauroyl sarcosinate (30% in water) | 8 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |

Example 7

| Composition | % |
|---|---|
| Purified water | QSAD 100 |
| Zinc coceth sulfate (25% in water) | 11 |
| Sodium lauroyl sarcosinate (30% in water) | 2.2 |
| Sodium lauroyl glutamate (37% in water) | 4.4 |
| Glycerin | 4 |
| Dipotassium glycyrrhizate | 0.25 |
| Zinc gluconate | 0.20 |
| PEG-200 hydrogenated glyceryl palmate and-PEG 7 glyceryl cocoate | 0.30 |
| PEG-75 | 2 |
| Sodium benzoate | 0.20 |
| Disodium EDTA | 0.10 |
| PEG-40 hydrogenated castor oil | 0.25 |
| Fragrance | 0.25 |
| Citric acid | 0.80 | pH = 4.13

Example 8

| Composition | % |
|---|---|
| Purified water | QSAD 100 |
| Sodium cocoyl isethionate (85% purity) | 1 |
| Zinc coceth sulfate (25% in water) | 10 |
| Glycerin | 4 |
| Dipotassium glycyrrhizate | 0.25 |
| Zinc gluconate | 0.20 |
| PEG-200 hydrogenated glyceryl palmate and PEG-7 glyceryl cocoate | 0.30 |
| PEG-75 | 2 |
| Disodium EDTA | 0.10 |
| Phenoxyethanol | 0.80 |
| Sodium benzoate | 0.20 |
| Citric acid | 0.15 | pH = 3.84

Example 9

| Composition | % |
|---|---|
| Purified water | QSAD 100 |
| Sodium methyl oleoyl taurate (63% purity) | 3 |
| Glycerin | 4 |
| Dipotassium glycyrrhizate | 0.25 |
| Zinc gluconate | 0.20 |
| Potassium Sorbate | 0.20 |
| Caprylyl glycol | 0.40 |
| PEG-75 | 2 |
| Sorbitan sesquicaprylate | 0.30 |
| Disodium EDTA | 0.10 |
| PEG-40 hydrogenated castor oil | 0.25 |
| Fragrance | 0.25 | pH = 5.58

Example 10

| Composition | % |
|---|---|
| Purified water | QSAD 100 |
| Sodium lauryl glucose carboxylate and lauryl glucoside (35% in water) | 5 |
| Glycerin | 4 |
| Dipotassium glycyrrhizate | 0.25 |
| Zinc gluconate | 0.20 |
| Potassium Sorbate | 0.80 |
| Phenoxyethanol | 0.20 |
| PEG-75 | 2 |
| Disodium EDTA | 0.10 | pH = 5.59

Example 11

| Composition | % |
|---|---|
| Purified water | QSAD 100 |
| Zinc coceth sulfate (25% in water) | 19.50 |
| Glycerin | 4 |
| Dipotassium glycyrrhizate | 0.50 |
| Zinc gluconate | 0.80 |
| PEG-200 hydrogenated glyceryl palmate and PEG-7 glyceryl cocoate | 0.30 |
| PEG-75 | 2 |
| Sodium Benzoate | 0.20 |
| Disodium EDTA | 0.10 |
| PEG-40 hydrogenated castor oil | 0.25 |
| Fragrance | 0.25 |

Example 12

| Composition | % |
|---|---|
| Purified water | QSAD 100 |
| Zinc coceth sulfate (25% in water) | 11 |
| Sodium lauroyl sarcosinate (30% in water) | 2.2 |
| Sodium lauroyl glutamate (37% in water) | 4.4 |
| Glycerin | 4 |
| Dipotassium glycyrrhizate | 0.15 |
| Zinc gluconate | 0.10 |
| PEG-200 hydrogenated glyceryl palmate and PEG-7 glyceryl cocoate | 0.30 |
| PEG-75 | 2 |
| Phenoxyethanol | 0.50 |
| Disodium EDTA | 0.10 |
| PEG-40 hydrogenated castor oil | 0.25 |
| Fragrance | 0.25 |
| Citric acid | 0.80 |

Example 13: In-Use Test to Assess Skin Barrier Damage Using the Composition According to the Invention Objective: In-use test to assess the cleansing performance of the foaming wash in acne subjects under anti-acne treatment.

Patients: 45 acne patients aged 12 to 45 years (78%: 12-19 years).

Protocol: The wash composition according to Example 1 was used twice daily, morning and night for four consecutive weeks.

Patients under anti-acne treatment also used a moisturiser once daily in the morning. Skin hydration was assessed by two different methods (TEWL, skin capacitance). Measurements were taken at baseline and after 7, 14 and 28 days of product use.

Results:

Relative to baseline TEWL did not change significantly during 14 days of use.

On day 28 there was a statistically significant decrease in TEWL relative to baseline ($p<0.05$).

There was no statistically significant change in skin capacitance, a direct measurement of skin hydration, during 28 days. Numerically skin hydration increased relative to baseline throughout the study.

Conclusions: In acne patients undergoing medical treatment, based on TEWL and hydration measurements, use of wash composition according to Example 1 does not induce skin barrier damage while cleansing

Example 14: In-Use Test to Assess Skin Surface Sebum Regulation Using the Composition According to the Invention Objective: In-use test to assess the effect of the test product on skin surface sebum levels in adult patients with mild-to-moderate acne, not undergoing anti-acne treatment.

Patients: 25 adult patients (18-35 years).

Protocol: Participants used the composition according to example 1 twice daily, morning and night for six consecutive weeks in conjunction with their usual moisturiser and make up. Change from usual products, or use of any medicated product for acne during the course of the study was not allowed. Sebumeter (Courage-Khazaka, SM 810, Germany) measurements were taken on the T-zone area across the forehead (2×2 cm squares) on days 14, 28, 42 and one week after completion of the trial on day 49.

Results:

There was a rapid and significant reduction in sebum levels immediately after first use of the product.

Sebum levels decreased throughout the study during 42 days relative to baseline.

On day 49, one week after use of the wash was stopped, sebum levels were the same as at baseline proving that there is no rebound effect.

Conclusion: Composition 1 is effective at reducing skin surface sebum levels immediately after use, a critical point in assessing the efficacy of a cleanser, and appears to control sebum surface levels when used daily. After one week follow-up there is no rebound effect.

Example 15: In-Use Test to Assess the Effect of the Composition According to the Invention on Skin pH Objective: In-use test to assess the effect of the test product on skin surface pH levels in adult patients with mild-to-moderate acne not undergoing anti-acne treatment.

Patients: 25 adult patients (18-35 years).

Protocol: Participants used the wash composition according to example 1 twice daily, morning and night for six consecutive weeks in conjunction with their usual moisturiser and make up. They were not allowed to change these products or use any medicated product for acne during the course of the study. pH measurements were taken in triplicate on the centre of the cheek using a pH meter (Courage-Khazaka, Germany) on days 14, 28, 42 and one week after completion of the trial on day 49.

Results: pH values remained constant throughout the trial period.

Conclusion: Use of composition 1 does not damage the skin barrier as evidenced by a stable skin surface pH over 6 weeks of use.

Example 16: Test to Measure the Sensitization Potential of the Composition According to the Invention Objective: To confirm that the composition according to example 1 does not produce allergic reactions on human skin under the maximised exposure conditions of this standard test.

Subjects: 215 healthy volunteers, aged between 18 and 65 (mean 45.5±11.7) years.

Protocol: During the challenge phase (3 weeks) test materials were applied three times per week under occlusion on the skin. Patches were removed after ~48-hours and any skin reaction was assessed visually on a scale of 1-5 at 48, 72 and 96 hours. The 2-week rest phase was followed by the 1-week's challenge phase, when test materials were applied again to the skin and a visual evaluation was performed at 48, 72 and 96 hours. Aqua demineata was used as the negative control.

Results:

No irritation was observed during the induction phase.

No allergic reactions were recorded.

Conclusion: the composition according to example 1 does not induce any allergic reaction nor does it demonstrate any sensitisation potential.

Example 17: Test to Confirm the Good Tolerability of the Composition According to the Invention Objective: To assess the tolerability of the foaming wash in acne subjects under antiacne treatment.

Patients: 91 acne patients aged 12 to 45 years (78%: 12-19 years).

Protocol: The composition according to example 1 was used twice daily, morning and night for four consecutive weeks.

Patients were under anti-acne treatment and used a moisturiser once daily in the morning. The skin was examined by a board-certified dermatologist at baseline and on subsequent visits (days 7, 14, 28). Subjects were asked to report any subjective irritation (itching, tightness, burning and stinging) they may have experienced on use of the test product.

Results:

No statistically significant changes relative to baseline, in erythema, oedema or roughness were observed by the dermatologist after 14 or 28 days of use.

No significant change, relative to baseline, in the degree of burning, itching, stinging or tightness were reported by the patients after 7, 14 or 28 days of use.

Conclusions: The data from both the dermatologist and subjects indicate that composition according to example 1 used in combination with a moisturizer (once-daily) is well tolerated and non-irritating in acne patients undergoing anti-acne treatment.

Example 18: Evaluation of the Comedogenicity of the Composition According to the Invention Objective: To evaluate the comedogenicity of a foaming face wash according to example 1 in adults with mild acne*.

Patients: 40 subjects with mild acne aged 18 to 35 years.

Protocol: The composition according to example 1 was used twice daily for four consecutive weeks. Comedogenicity was assessed by acne lesion counts (open and closed comedones, papules and pustules) performed by an experienced clinical grader.

Results:
After 28 days of use there was a significant improvement in non-inflammatory (open and closed comedones) acne lesion counts compared with baseline.
There were no significant changes in inflammatory (papules and pustules) or whole face total (inflammatory and non-inflammatory) acne lesion counts after 28 days of use.

Conclusions: The composition according to example 1 appears to be non-comedogenic and effective in improving comedone lesion counts.

Example 19: Evaluation of the Cosmetic Acceptability of the Composition According to the Invention Objective: In-use test to assess the cosmetic acceptability of the foaming wash composition according to the example 1 in acne subjects under anti-acne treatment.

Patients: 91 acne patients aged 12 to 45 years (78%: 12-19 years).

Protocol: The wash was used twice daily for four consecutive weeks, morning and night and rinsed with water. Patients were under anti-acne treatment and used a moisturiser once daily in the morning. Participants completed a questionnaire after 28 days of use.

Results: After 28 days of use there was a significant proportion ($P \leq 0.05$) of the subjects testing the foaming wash that felt that the product was easy to use, soothed their skin from the irritation of anti-acne treatment, provided a clean healthy feeling, was easy to incorporate into their daily skin care routine and would recommend the wash to their family and friends.

Conclusions: Acne patients formed a very positive opinion of the composition of example 1 according to the invention. They found it pleasant and easy to use, it soothed their skin from the irritation of anti-acne treatment and helped it appear less greasy. The wash was cosmetically acceptable and easy to incorporate into daily skin care routines.

The invention claimed is:

1. A foaming topical wash composition consisting of:
(a) between 1% and 10% by weight of zinc coceth sulfate of active material (AM) relative to the total weight of the composition;
(b) between 0.15% and 0.3% by weight of zinc gluconate relative to the total weight of the composition; and
(c) between 0.25% and 0.3% by weight of dipotassium glycyrrhizate relative to the total weight of the composition; and
(d) one or more pharmaceutically acceptable excipients selected from the group consisting of: (i) gelling agents; (ii) viscosity increasing agents; (iii) emulsifiers; (iv) antioxidants selected from the group consisting of vitamin E and its derivatives, vitamin C and its derivatives, butylated hydroxytoluene, butylated hydroxyanisole, acetyl cysteine, citric acid, sodium metabisulfite, sodium sulfite, and combinations thereof; (v) vitamins and/or vitamin derivatives selected from the group consisting of vitamin E and its derivatives, vitamin C and its derivatives, vitamin B3, niacinamide, and combinations thereof; (vi) soothing agents and/or anti-irritants selected from the group consisting of PPG-12/SMDI copolymer, allantoin and its derivatives, hyaluronic acid, polyquaternium-51, D-panthenol, and aloe vera; (vii) lecithins and/or phospholipids; (viii) cholesterol and/or cholesterol derivatives; (ix) preservatives; (x) acids and/or bases; (xi) chelating agents; (xii) humectants; (xiii) wetting agents; (xiv) foam boosters; (xv) ingredients providing a smoothness of the foam; (xvi) perfume solubilizing agents; (xvii) perfumes and/or fragrances; (xviii) refatting agents; (xix) mineral, synthetic, or silicone oils; and (xx) water,
wherein the foaming topical wash composition does not contain ethanol.

2. The topical wash composition according to claim 1, wherein the concentration of zinc gluconate is 0.20%.

3. The topical wash composition according to claim 1, wherein the concentration of dipotassium glycyrrhizate is 0.25%.

4. The topical wash composition according to claim 1, wherein the pH of the topical wash composition is from about 3 to about 6.

5. The topical wash composition according to claim 1, wherein the pH of the topical wash composition is from about 3.5 to about 5.0.

6. The composition of claim 1, wherein the gelling agents are selected from the group consisting of microcrystalline cellulose, sodium carboxymethylcellulose, hydroxypropylmethylcellulose, carbomers, polysaccharides, magnesium aluminum silicate, sodium magnesium silicate, sodium magnesium fluorosilicate, magnesium sodium silicate, tetrasodium pyrophosphate, the family of acrylic polymers, acrylate copolymers, polyacrylate-13/polyisobutylene/polysorbate-20, gelling agents of the polyacrylamide family, the family of modified starches, and mixtures thereof.

7. The composition of claim 1, wherein the viscosity increasing agents are selected from the group consisting of sodium chloride, PEG-120 methyl glucose dioleate, PEG-200 hydrogenated glyceryl palmate, PEG-7 glyceryl cocoate, ceteareth-60 myristyl glycol, and combinations thereof.

8. The composition of claim 1, wherein the lecithins and/or phospholipids are selected from the group consisting of phosphatidyl choline, phosphatidyl inositol, phosphatidyl ethanolamine, phosphatidic acid, Phospholipon 90H, and mixtures thereof.

9. The composition of claim 1, wherein the preservatives are selected from the group consisting of benzalkonium chloride, bronopol, chlorhexidine, chlorocresol and its derivatives, phenoxyethanol, potassium sorbate, sodium benzoate, diazolidinylurea, benzyl alcohol, parabens, and mixtures thereof.

10. The composition of claim 1, wherein the acids and/or bases are selected from the group consisting of citric acid, lactic acid, sodium citrate, triethanolamine, aminomethyl propanol, sodium hydroxide, diisopropanolamine, and mixtures thereof.

11. The composition of claim 1, wherein the humectants are selected from the group consisting of propylene glycol, glycerin, pentylene glycol, 1-2 hexanediol, caprylyl glycol, and mixtures thereof.

12. The composition of claim 1, wherein the wetting agents are selected from the group consisting of poloxamers, glycols, sodium docusate, and mixtures thereof.

13. The composition of claim 1, wherein the ingredients providing a smoothness of the foam are selected from the group consisting of PEG-7 glyceryl cocoate, PEG-200 hydrogenated glyceryl palmate, polypropylene terephthalate, C12-13 alkyl lactate, and combinations thereof.

14. The composition of claim 1, wherein the foam boosters are selected from the group consisting of polyethylene glycols, glycerylmonocaprylate, cocamidopropyl hydroxysultaine, sorbitan sesquicaprylate, and combinations thereof.

15. The composition of claim 1, wherein the perfume solubilizing agents are selected from PEG-40 hydrogenated castor oil, PEG-60 hydrogenated castor oil, polysorbate 80, polysorbate 20, and mixtures thereof.

16. The composition of claim 1, wherein the refatting agents are selected from coco-glucoside, glyceryl oleate, and PEG-6-caprylic/capric glycerides, and mixtures thereof.

17. The topical wash composition according to claim 1, consisting of:

| | |
|---|---|
| Purified water | QSAD 100 |
| Zinc coceth sulfate (25% in water) | 19.50% |
| Glycerin | 4% |
| Dipotassium glycyrrhizate | 0.25% |

-continued

| | |
|---|---|
| Zinc gluconate | 0.20% |
| PEG-200 hydrogenated glyceryl palmate and PEG-7 glyceryl cocoate | 0.30% |
| PEG-75 | 2% |
| Sodium benzoate | 0.20% |
| Disodium EDTA | 0.10% |
| PEG-40 hydrogenated castor oil | 0.25%, and |
| Fragrance | 0.25%. |

18. A method of cleansing or washing the skin of an acne patient, the method comprising cleansing or washing the skin of the patient in need thereof with the topical wash composition according to claim 1, wherein the patient is under active treatment or in long-term maintenance.

19. A method of washing acne skin, the method comprising washing the acne skin of a patient in need thereof with the topical wash composition according to claim 1, wherein a barrier function of the skin is kept intact.

20. A method of regulating sebum production in skin of an acne patient, the method comprising regulating sebum production in the skin of the acne patient in need thereof with the topical wash composition according to claim 1.

21. A method for improving acne skin, the method comprising administering to the acne skin of an individual subject in need thereof an effective amount of the topical wash composition according to claim 1.

* * * * *